United States Patent [19]

Sabourin

[11] Patent Number: 5,408,884
[45] Date of Patent: Apr. 25, 1995

[54] APPARATUS AND METHOD FOR ULTRASONIC RECONSTRUCTION AND TESTING OF A TURBINE ROTOR BLADE ATTACHMENT STRUCTURE

[75] Inventor: Paul F. Sabourin, Charlotte, N.C.

[73] Assignee: Electric Power Research Institute, Inc., Palo Alto, Calif.

[21] Appl. No.: 163,136

[22] Filed: Dec. 6, 1993

[51] Int. Cl.⁶ .......................................... G01N 29/04
[52] U.S. Cl. ...................................... 73/649; 73/620; 73/623
[58] Field of Search .................. 73/649, 619, 620, 621, 73/628, 633, 641, 602, 618

[56] References Cited

U.S. PATENT DOCUMENTS

| | | | |
|---|---|---|---|
| 3,918,295 | 11/1975 | Herbertz | 73/67.7 |
| 4,241,608 | 12/1980 | Dees et al. | 73/606 |
| 4,354,388 | 10/1982 | Diepers et al. | 73/628 |
| 4,441,369 | 4/1984 | Lessard et al. | 73/602 |
| 4,624,143 | 11/1986 | Green | 73/620 |
| 4,966,746 | 10/1990 | Richardson et al. | 376/249 |
| 5,009,105 | 4/1991 | Richardson et al. | 73/621 |
| 5,074,677 | 12/1991 | Andree et al. | 384/448 |
| 5,111,696 | 5/1992 | Lurd et al. | 73/627 |

FOREIGN PATENT DOCUMENTS 0157302 10/1985 European Pat. Off. .............. 73/619

Primary Examiner—Hezron E. Williams
Assistant Examiner—Helen C. Kwok
Attorney, Agent, or Firm—Flehr, Hohbach, Test, Albritton & Herbert; William S. Galliani

[57] ABSTRACT

An apparatus and method for ultrasonic reconstruction and testing of a non-visible turbine rotor blade attachment structure is described. The method of the invention includes positioning transducers at a first location to obtain slot region scan data corresponding to a slot region of the non-visible turbine rotor blade attachment structure, and positioning transducers at a second location to obtain straddle-mount region scan data corresponding to a straddle-mount region of the non-visible turbine rotor blade attachment structure. The shape of the non-visible turbine rotor blade attachment structure is reconstructed from the slot region scan data and the straddle-mount region scan data to form reconstruction data. The reconstruction data is used to select test scan positions for ultrasonic testing. Ultrasonic testing is then performed at the selected test scan positions.

16 Claims, 9 Drawing Sheets

APPARATUS AND METHOD FOR ULTRASONIC RECONSTRUCTION AND TESTING OF A TURBINE ROTOR BLADE ATTACHMENT STRUCTURE

BRIEF DESCRIPTION OF THE INVENTION

This invention relates generally to the non-destructive evaluation of turbine parts. This invention more particularly relates to an ultrasound apparatus that is used to reconstruct a non-visible straddle-mount rotor blade attachment structure, thereby allowing subsequent ultrasonic testing of the structure.

BACKGROUND OF THE INVENTION

Turbines are used for generating rotary mechanical power from the energy in a working fluid. The working fluid energy, originally in the form of pressure energy, is converted to velocity energy by passing through a system of blades in the turbine. Changes in the magnitude and direction of the velocity energy are made to cause tangential forces on the blades, producing mechanical rotation of a turbine rotor. The rotating turbine rotor may be positioned to interact with a generator rotor and generator stator and thereby produce electricity.

FIG. 1 is a simplified illustration of a rotor assembly 20 that includes a rotor shaft 22 supporting a number of blade assemblies 24A, 24B, 24C, 24D. Each blade assembly 24 includes a blade hub 26A that supports a number of blades 28.

A rotor blade attachment structure, to be described below, couples the blade hub 26A with the blades 28. The attachment structure requires periodic inspection to detect service induced flaws. As used herein, service induced flaws refer to any type of flaw that may initiate during the operation of a turbine rotor, including stress corrosion cracking, creep fatigue cracking, fatigue cracking, pits, and other imperfections generally arising from stress and exposure to corrosive environments.

If the blades 28 are removed from the hub 26A, the geometry of the attachment structure is exposed. Consequently, service induced flaws may be identified by liquid penetrant, magnetic particle, and eddy current inspection techniques. These techniques may also be used when the blades do not entirely cover the attachment region structure.

A widely used rotor blade attachment structure is the straddle-mount design. In the straddle-mount design, the blade straddles the entire attachment structure. As a result, surface inspections can only be conducted with the blades removed, a time-consuming and expensive task.

FIG. 2 shows a straddle-mount rotor blade attachment architecture 29. The straddle-mount rotor blade attachment architecture 29 includes a slot region 30, with a number of slots 31A, 31B, and a straddle-mount region 32 including a number of hooks 33A, 33B. FIG. 2 also depicts individual blades 28A, 28B. Each blade 28 includes a blade interlock structure (34A or 34B) and a blade face (36A or 36B).

It can be appreciated from FIG. 2 that a blade interlock structure (34A or 34B) is fitted over the slot region 30 and is then moved to the straddle-mount region 32 where it forms a secure fit with the straddle-mount region 32 hooks 33A, 33B. In this way, blades 28 are positioned around the entire periphery of the blade hub 26. The last blade 28 placed on the hub 26 is positioned at the slot region 30 and is secured at the slot region by pinning it to the blade hub or attaching it to adjacent blades.

FIG. 3 is an enlarged perspective view of a straddle-mount rotor blade attachment structure. The figure more particularly illustrates the nature of the straddle-mount region 32 and its corresponding hooks 33A, 33B. The figure also illustrates the slot region 30 and its slots 31A, 31B. As used herein, the straddle-mount region 32 and the slot region 30 include the shaped perimeter of the blade hub 26 and the regions adjacent thereto.

FIG. 4 is a cross-sectional view of the slot region 30 of a straddle-mount attachment structure. FIG. 5 is a cross-sectional view of the straddle-mount region 32 of a straddle-mount attachment architecture. The corresponding blade 28 for each attachment architecture region is omitted from FIGS. 4 and 5.

FIG. 5 also shows a number of ultrasound transducers 40A, 40B, 40C respectively placed at positions P1, P2, and P3. The transducers 40A, 40B, 40C are used to test the straddle-mount attachment structure for service induced flaws.

Ultrasonic testing procedures are commonly used to examine turbine components for the purpose of detecting and characterizing service induced flaws. The technique involves applying high frequency sound waves to a structure of interest. When the sound waves interact with an object that has a significant difference in acoustic impedance (the product of density and velocity) from that of the propagation medium, a portion of the sound is either reflected or diffracted back to the source from which the sound originated. Measurement and evaluation of the returned sound pattern permits determination of the presence and characteristics of the reflecting medium.

For ultrasonic techniques to work it is necessary to discriminate between object architecture and flaws in the object architecture. This discrimination is readily accomplished when the object architecture is known. In the case of straddle-mount rotor blade attachment structures, only the manufacturer knows the precise structure architecture. Thus, only a manufacturer is aware of the proper positions for the transducers used in ultrasonic testing, for example, positions P1, P2, and P3 in FIG. 5. Manufacturers are reluctant to disclose this information because it is generally considered a trade secret. In the absence of information regarding attachment architecture, it is difficult to discriminate between service induced flaws and attachment architecture. Thus, it would be highly desirable to provide a method and apparatus for physically characterizing a non-visible rotor blade attachment structure. This information could then be used to perform ultrasonic testing of the rotor blade attachment structure.

SUMMARY OF THE INVENTION

An apparatus and method for ultrasonic reconstruction and testing of a non-visible turbine rotor blade attachment structure is described. The method of the invention includes positioning transducers at a first location to obtain slot region scan data corresponding to a slot region of the non-visible turbine rotor blade attachment structure, and positioning transducers at a second location to obtain straddle-mount region scan data corresponding to a straddle-mount region of the non-visible turbine rotor blade attachment structure. The shape of the non-visible turbine rotor blade attachment structure is reconstructed from the slot region scan data and the straddle-mount region scan data to form reconstruction data. The reconstruction data is used to select test scan positions for ultrasonic testing. Ultrasonic testing is then performed at the selected test scan positions.

BRIEF DESCRIPTION OF THE DRAWINGS

For a better understanding of the nature and objects of the invention, reference should be made to the following detailed description taken in conjunction with the accompanying drawings, in which.

Like reference numerals refer to corresponding parts throughout the several views of the drawings.

DETAILED DESCRIPTION OF THE INVENTION

Figure 1:
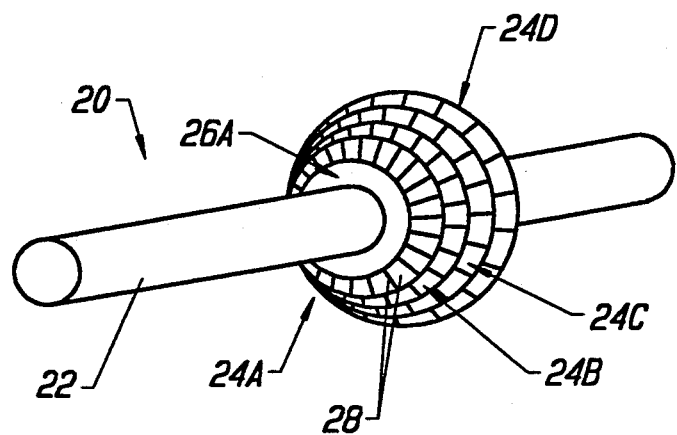
FIG. 1 is a perspective view of a rotor assembly.
Figure 2:
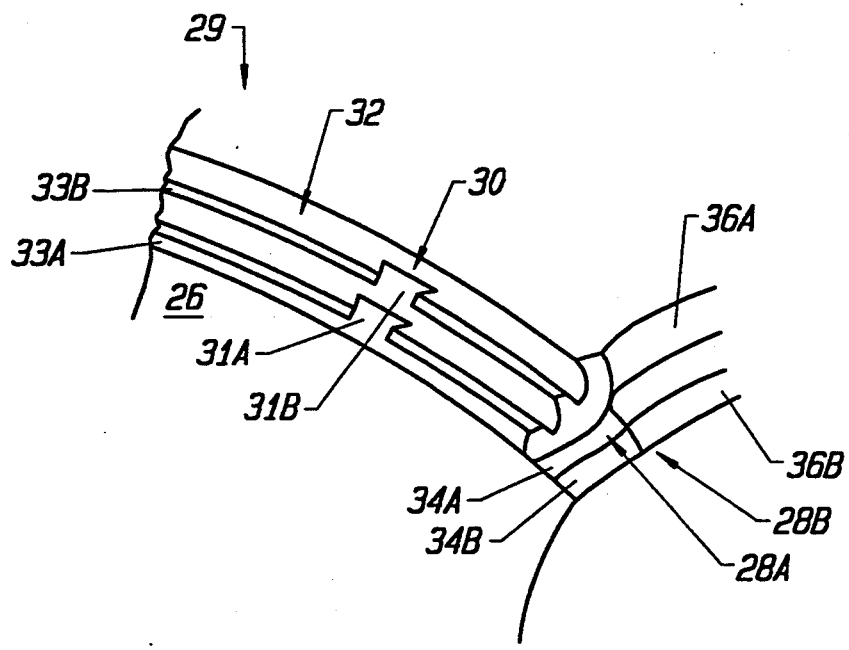
FIG. 2 is a perspective view of a straddle-mount rotor blade attachment structure.
Figure 3:
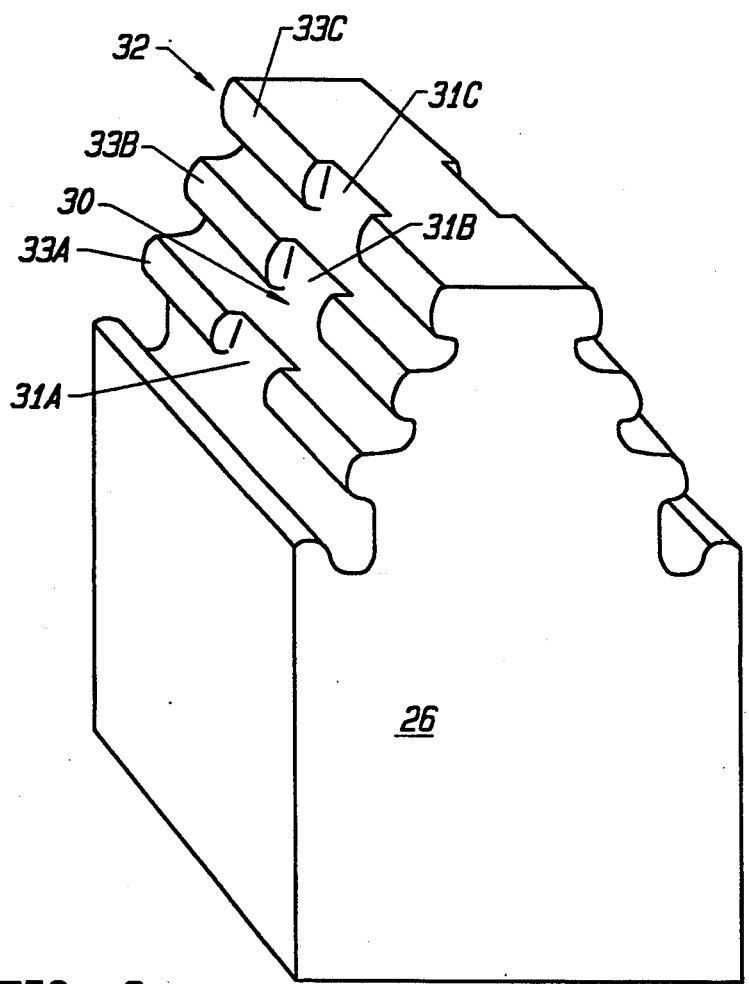
FIG. 3 is an enlarged perspective view of a straddle-mount rotor blade attachment structure.
Figure 4:
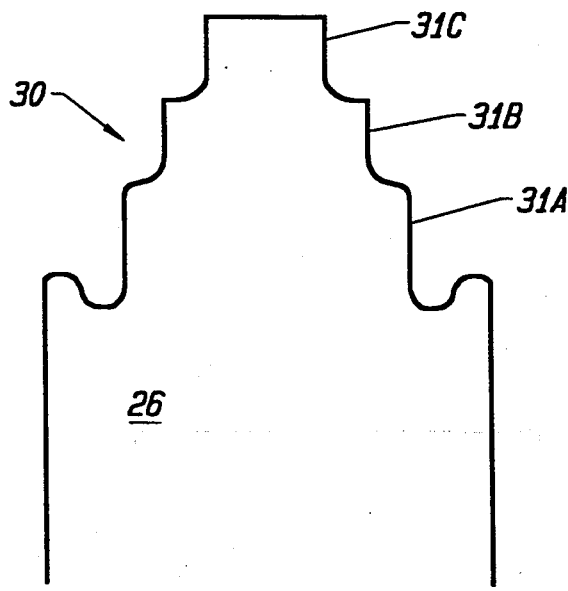
FIG. 4 is a cross-sectional view of a slot region of a straddle-mount rotor blade attachment structure.
Figure 5:
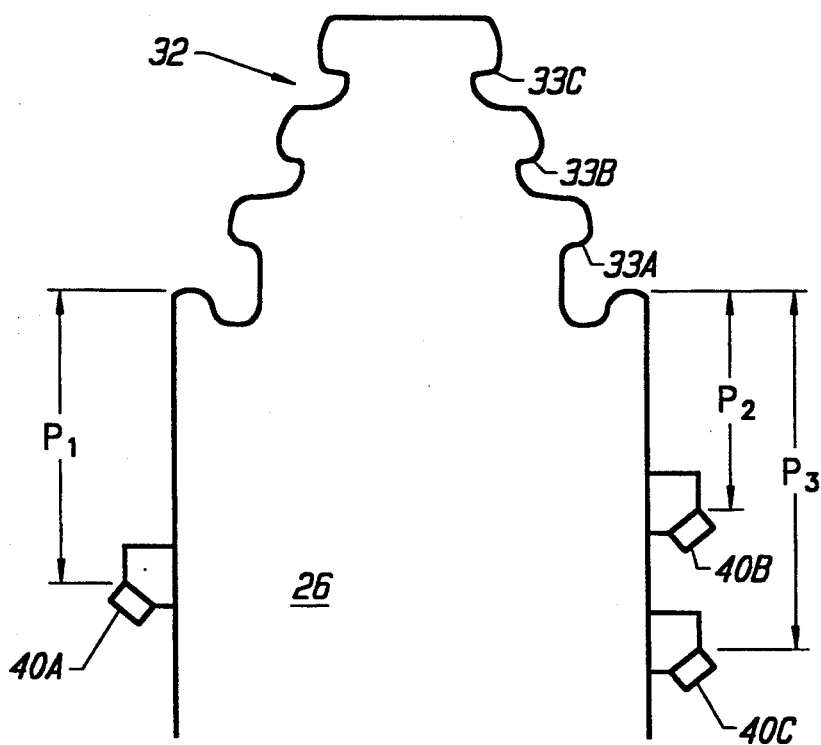
FIG. 5 is a cross-sectional view of a straddle-mount region of a straddle-mount rotor blade attachment structure.
Figure 6:
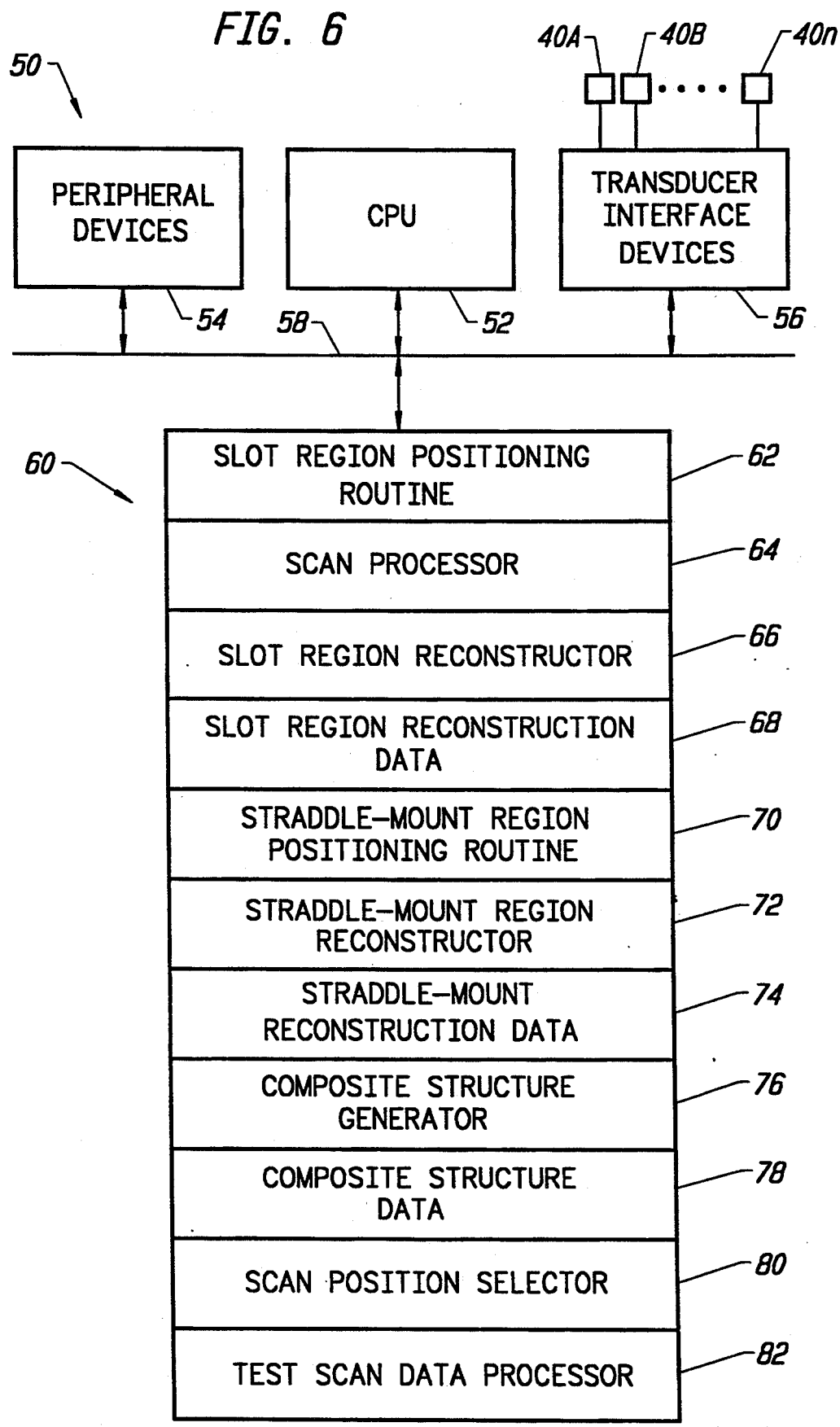
FIG. 6 illustrates the ultrasonic reconstruction and testing apparatus of the invention.

FIG. 6 illustrates the ultrasonic reconstruction and testing apparatus 50 of the invention. The device 50 includes a central processing unit (CPU) 52 that communicates with peripheral devices 54, transducer interface devices 56, and memory unit 60 over bus 58. The CPU 52 may be a general purpose computing unit and the peripheral devices 54 may be standard input/output devices such as a keyboard, mouse, video monitor, and printer. The transducer interface devices 56 include standard analog-to-digital elements that couple transducers 40 to a CPU 52. As will be discussed below, the transducer interface devices 56 also include physical movement devices for altering the linear and angular positions of the transducers. The memory module 60 may be any combination of disc, RAM, and ROM storage.

The elements described up to this juncture, and their interaction, are known in the art. Attention therefore turns to the execution programs stored in memory module 60. The execution programs in memory 60 force the various components of the invention to operate in a novel manner so as to generate reconstruction data for a non-visible straddle-mount rotor blade attachment structure and then to use this information to perform subsequent ultrasonic testing of the non-visible straddle-mount rotor blade attachment structure. The execution programs of the invention include a slot region positioning routine 62, a scan processor 64, a slot region reconstructor 66, a straddle-mount region positioning routine 70, a straddle-mount region reconstructor 72, a composite structure generator 76, a scan position selector 80, and a test scan data processor 82.

Figure 7:
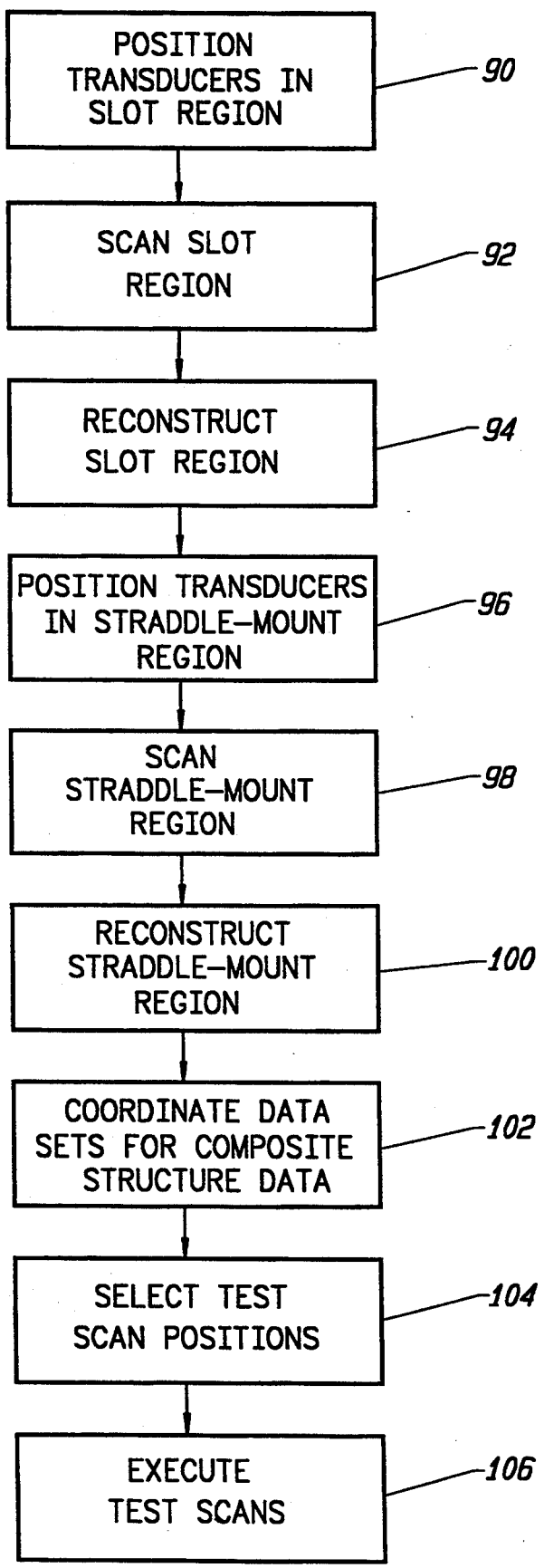
FIG. 7 illustrates the ultrasonic reconstruction and testing method of the invention.

The steps associated with the method of the invention are described in relation to FIG. 7. The first step associated with the method of the invention is to position ultrasound transducers in the slot region of a selected blade assembly (block 90). The original positioning of the transducers may be done manually or by relying upon a slot region positioning routine 62.

Figure 8:
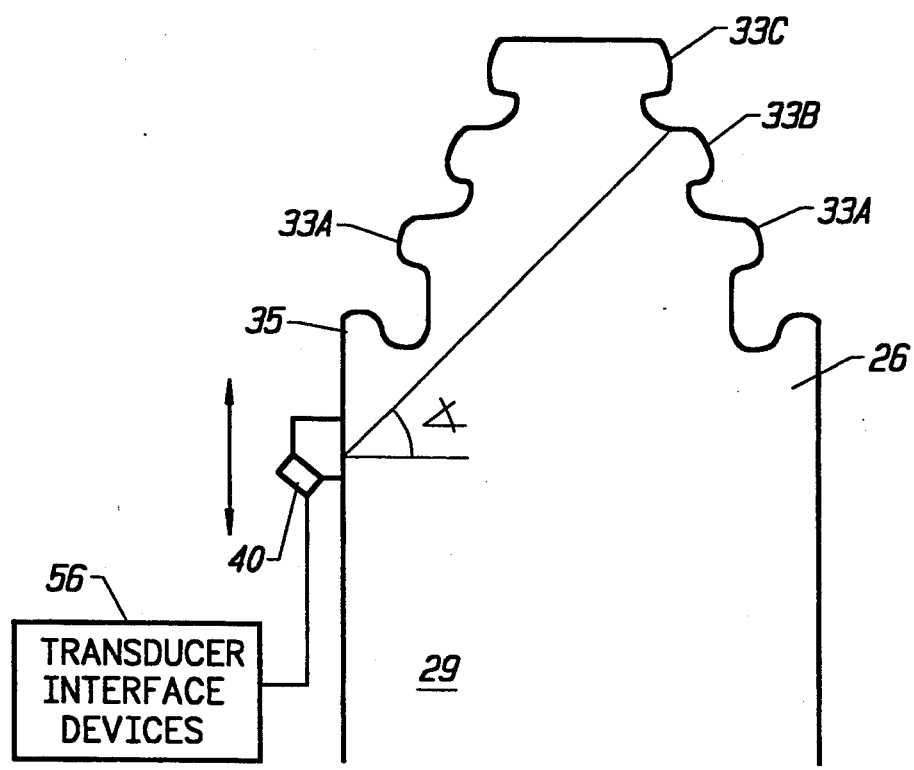
FIG. 8 illustrates the scan motion of an ultrasonic transducer utilized in accordance with the invention.

FIG. 8 is a cross-sectional view of a transducer 40 positioned in the straddle-mount region 32 of a rotor blade attachment structure 29. The slot region positioning routine 62 receives positional commands through a peripheral device 54 and converts the positional commands to control signals that are applied to the transducer interface devices 56. The transducer interface devices include movement devices for the transducers and encoding devices for governing the motion of the movement devices. For example, a linear movement device may be in the form of a lead screw. In this case, the transducers 40 are positioned on the lead screw and an encoder and a lead screw drive mechanism are used to position the transducer 40 a selected distance from a given hook 33 or tang 35 of the rotor blade attachment structure 29.

The next step associated with the method of the invention is to scan the slot region (block 92). The arrow in FIG. 8 shows the direction (radial) of the scan motion. The scan processor 64 generates control signals for the transducer interface devices 56 such that the ultrasound transducer 40 is moved in a radial direction from its original position.

Preferably, the scanning step includes at least two scans. One scan is performed with the ultrasonic transducer 40 producing a signal with an angle of approximately 60°. Afterwards, the transducer is returned to its original position and the angle of the transducer is changed to approximately 40°. The change in angle orientation of the transducer may be accomplished through an angular movement device, such as a solenoid. The angular movement device operates under the control of the scan processor 64 which generates signals that are applied to the transducer interface devices 56.

A signal is transmitted from one side of the blade hub 26 to an opposite side of the blade hub 26. The signal angle is measured from a horizontal plane, as indicated in FIG. 8. Multiple scans are preferred because a shallow angle (40°) may not be sufficient to obtain a return signal from the top hook 33C or slot 31C, while the steep angle (60°) requires a large radial displacement to obtain a return signal from the bottom hook 33A or slot 31A.

The next step associated with the method of the invention is to reconstruct the slot region (block 94). This may be performed by a slot region reconstructor 66 which is a sequence of computer code for receiving and processing the accumulated slot region scan data. The slot region scan data includes data describing the linear (radial) position of the transducer 40, the reconstruction signal propagation time, and the scan angle. As used herein, the reconstruction signal refers to the echo signals received at the transducer 40 that correspond to surface discontinuities formed at the interface between the blade interlock structure 34 and the blade attachment structure 29.

The slot region reconstructor 66 groups all data with the same scan angle. If two scan angles are used, say 40° and 60° then the slot region reconstructor compares the two sets of data by radial position. If one set of data has a reconstruction signal for a given radial position and the other set of data does not, then the existing signal value is added to a combined data file representing the slot region reconstruction data. If at another radial position one set of data has a first reconstruction signal value and the second set of data has a second reconstruction signal value, then the first and second reconstruction signal values are averaged. The averaged value is then added to the combined data file representing the slot region reconstruction data.

Figure 9:
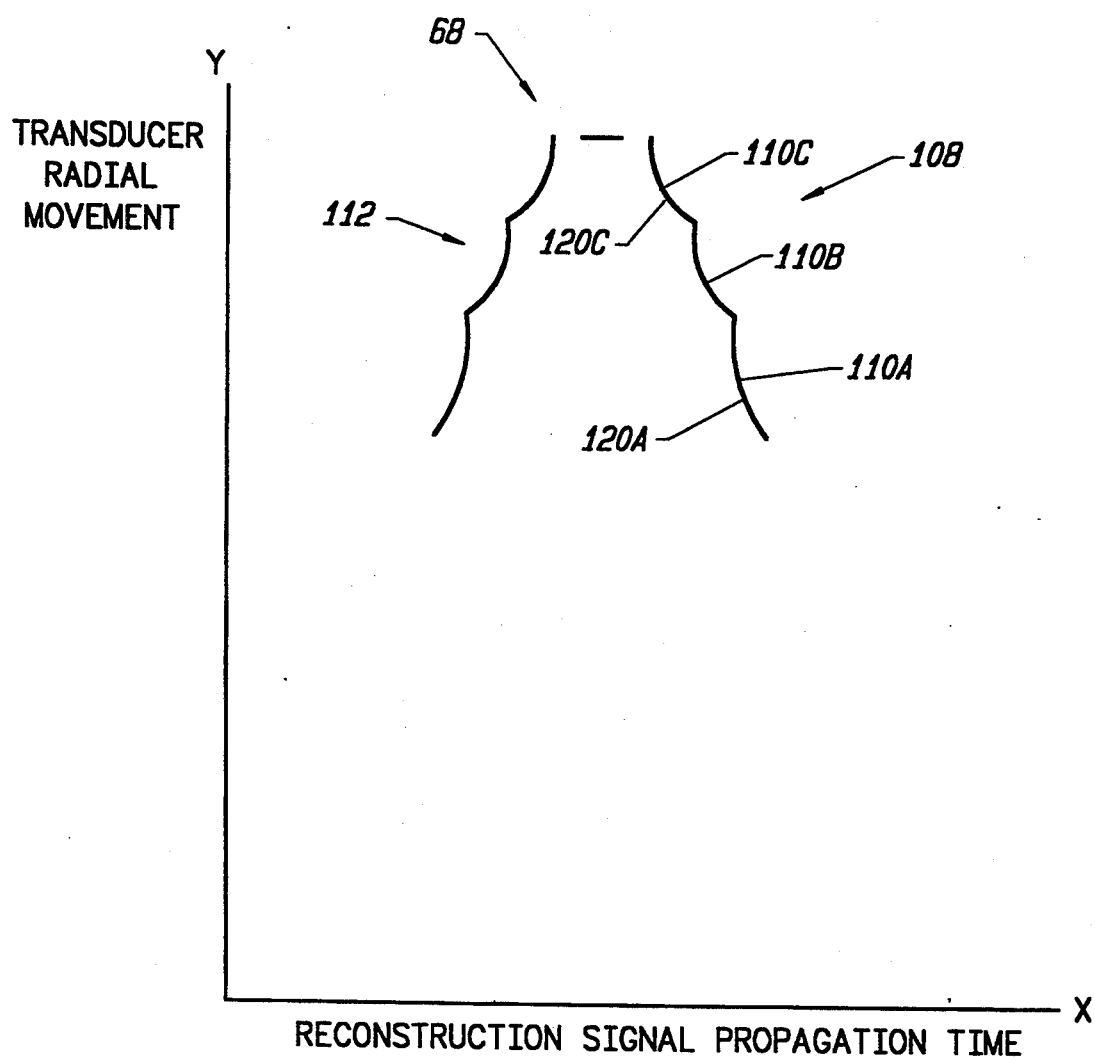
FIG. 9 depicts slot region reconstruction data that is generated in accordance with the invention.

The reconstructed data may be in the form of a data file or it may be a data plot exhibited on a peripheral device 54, such as a video monitor or a printer. The curve 108 in FIG. 9 illustrates plotted data received from a transducer positioned on the left side of a blade hub, as shown in FIG. 8 (however, note that FIG. 8 depicts a straddle-mount region, not a slot region, as is being discussed at this time). The x-axis plots the radial movement of the transducer 40. Line segment 110C corresponds to the highest slot 31C of the blade attachment structure. Note that as the transducer moves away from its original position proximate to the tang 35, data is collected regarding the lower slots 110B, 110A of the attachment structure. The y-axis plots the propagation time for the reflected reconstruction signal. Line segment 110C in FIG. 9 corresponds to the top slot 31C of the blade attachment structure 29. Note the large time propagation associated with the top slot 110C, corresponding to the furthest distance that the ultrasound signal must travel for the particular architecture.

Curve 112 in FIG. 9 corresponds to slot region scan data accumulated by the transducer positioned on the right side of the blade hub 26. The curve 112 has the same characteristics and may otherwise be interpreted in the same manner as curve 108. Note that the curves 108 and 112 generally reconstruct the slot region 30 of the straddle-mount blade attachment structure 29. As will be discussed below, this information may be used for subsequent ultrasonic test scanning of the slot region 30.

The next step associated with the invention is to position transducers in the straddle-mount region (block 96). Again, this may be done manually or through the use of a straddle-mount region positioning routine 70. The straddle-mount region positioning routine 70 operates in the same manner as the previously described slot region positioning routine 62.

The next step associated with the method of the invention is to scan the straddle-mount region (block 98). As previously described, the scanning operation is preferably performed at a number of scan angles. The operation of the movement devices is coordinated by the scan processor 64.

Figure 10:
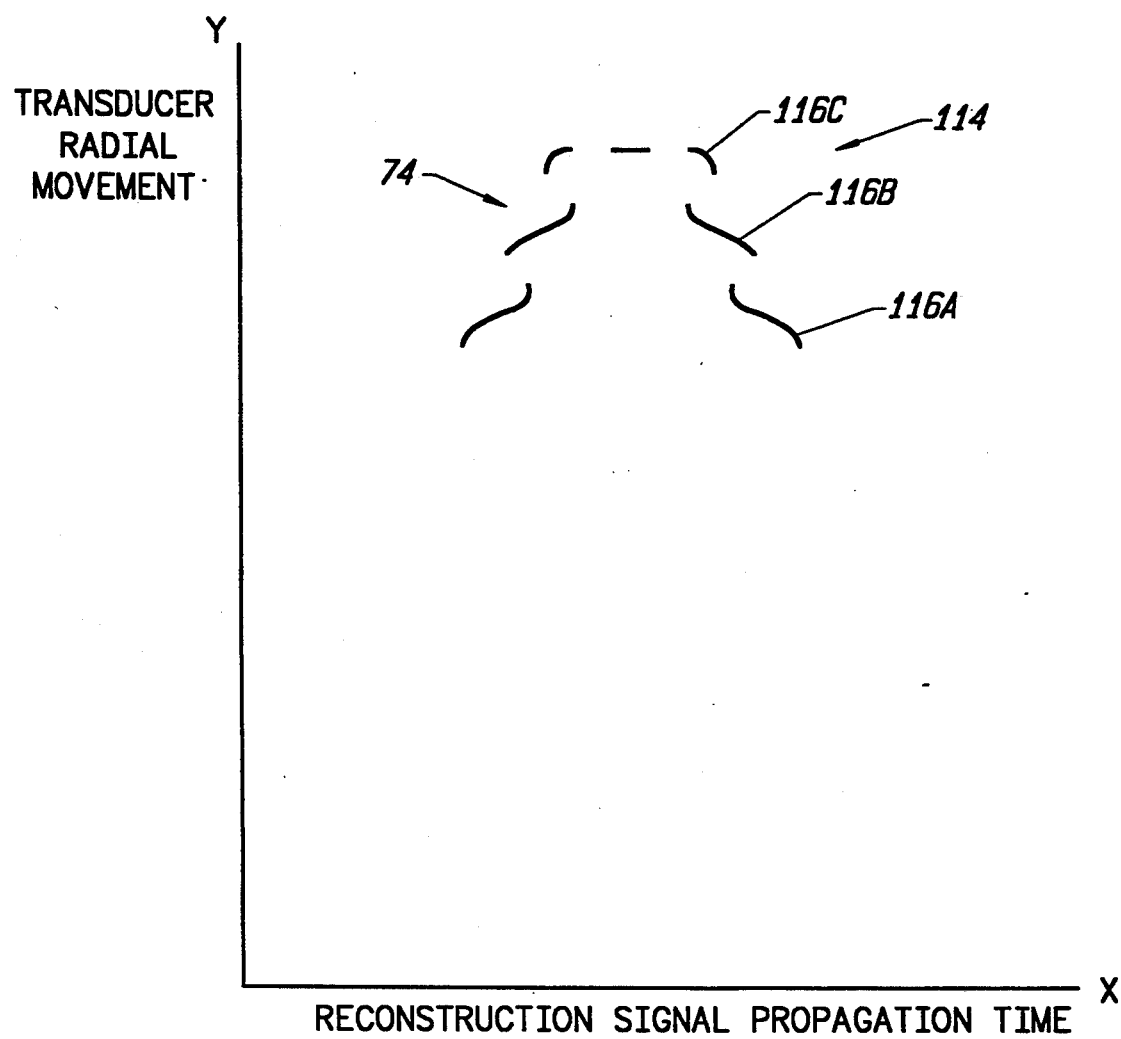
FIG. 10 depicts straddle-mount reconstruction data that is generated in accordance with the invention.

Next, the apparatus of the invention reconstructs the straddle-mount region (block 100). This operation is performed by the straddle-mount reconstructor (block 72). The straddle-mount reconstruction operation is performed in the same fashion as the slot region reconstruction operation previously described. FIG. 10 depicts a plot of reconstructed straddle-mount data.

The discontinuous curve 114 on the right side of FIG. 10 corresponds to data obtained from a transducer positioned on the left side of the blade attachment structure 29. Line segment 116C corresponds to the top hook 33C of the blade attachment structure 29, while line segment 116A corresponds to the bottom hook 33C of the blade attachment structure 29. Line segment 116B corresponds to the middle hook 33B of the blade attachment structure 29.

The next step associated with the invention is to coordinate the reconstruction straddle-mount data and the slot region reconstruction data to form composite structure data (block 102). The composite structure data 78 represents a complete description of the straddle-mount region 32.

Figure 11:
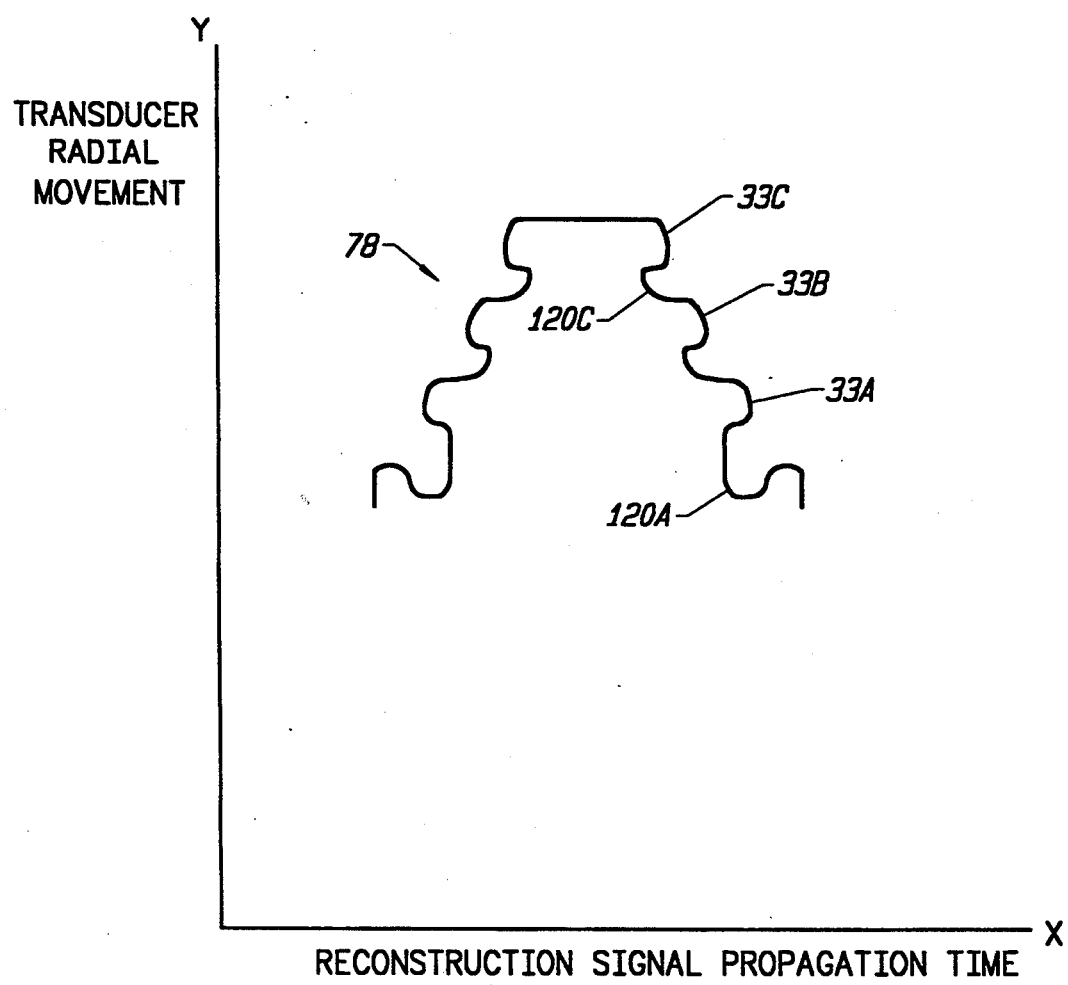
FIG. 11 depicts composite structure data that is generated in accordance with the invention.

The composite structure data is generated by the composite structure generator 76. For each radial position, the composite structure generator 76 obtains corresponding values from both the slot region reconstruction data 68 and the straddle-mount reconstruction data 74. The straddle-mount reconstruction data includes most information required for the composite structure data 78. However, the slot region reconstruction data 68 is used to confirm the interior position 120A, 120C of each hook 33 and to otherwise corroborate the accuracy of the straddle-mount reconstruction data 74. The slot region reconstruction data corresponding to slot regions 110A, 110B, 110C is ignored by the composite structure generator 76. FIG. 11 depicts plotted composite structure data 78.

The next step associated with the method of the invention is to select test scan positions (block 104). This operation relies upon the composite structure data 78 when selecting scan positions for the straddle-mount region 32 and the slot region reconstruction data when selecting scan positions for the slot region 30. The straddle-mount region reconstruction data may also be used in selecting scan positions, although relying upon the composite structure data is preferable. Once information is available regarding a straddle-mount architecture, there are known techniques for selecting test scan positions. Such criteria is incorporated into the scan position selector 80. In other words, based upon the straddle-mount architecture as defined by the composite structure data 78, the scan position selector 80 utilizes known guidelines to identify transducer positions for undertaking ultrasonic testing functions.

The final step associated with the invention is to execute test scans (block 106). This operation is performed under the direction of the test scan data processor 82. The test scan data processor applies signals to the transducer interface devices to move the transducers to the selected scan positions. The test scan data processor then initiates scanning operations and processes the test scan data in accordance with prior art techniques.

One skilled in the art will appreciate the importance of the present invention's ability to reconstruct a non-visible straddle-mount structure. This feature allows subsequent ultrasonic testing of the straddle-mount structure while the blades are still in position. The ability to ultrasonically test a rotor blade attachment structure with the blades in place saves time and money. The ability to reconstruct the straddle-mount structure without the benefit of design drawings allows parties other than the manufacturer of the rotor assembly to test and maintain a rotor assembly.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following Claims and their equivalents.

I claim:

1. An apparatus for ultrasonic reconstruction and testing of a non-visible turbine rotor blade attachment structure, said apparatus comprising:
   a plurality of ultrasound transducers;
   a plurality of transducer interface devices for positioning said plurality of ultrasound transducers;
   means for generating command signals for said transducer interface devices so as to locate said ultrasound transducers at a plurality of scan positions;
   means for accumulating reconstruction data from said plurality of ultrasound transducers at said plurality of scan positions, said reconstruction data corresponding to the shape of said non-visible turbine rotor blade attachment structure; and
   means for selecting test scan positions based upon said reconstruction data.

2. The apparatus of claim 1 wherein said non-visible turbine rotor blade attachment structure is a straddle-mount rotor blade attachment structure including a slot region and a straddle-mount region.

3. The apparatus of claim 2 wherein said accumulating means includes:
   means for obtaining slot region reconstruction data corresponding to the shape of said slot region; and
   means for acquiring straddle-mount reconstruction data corresponding to the shape of said straddle-mount region.

4. The apparatus of claim 3 wherein said accumulating means includes:
   means for deriving composite structure data corresponding to said straddle-mount region, said deriving means deriving said composite structure data from said straddle-mount reconstruction data and said slot region reconstruction data, said slot region reconstruction data being used by said deriving means to confirm the accuracy of said straddle-mount reconstruction data.

5. A method of ultrasonic reconstructing and testing of a non-visible turbine rotor blade attachment structure, said method comprising the steps of:
   locating a plurality of ultrasound transducers at a plurality of scan positions;
   accumulating reconstruction data from said plurality of ultrasound transducers at said plurality of scan positions, said reconstruction data corresponding to the shape of said non-visible turbine rotor blade attachment structure;
   selecting test scan positions based upon said reconstruction data; and
   performing ultrasonic testing of said turbine rotor blade attachment structure at said test scan positions.

6. The method of claim 5 wherein said non-visible turbine rotor blade attachment structure is a straddle-mount rotor blade attachment structure including a slot region and a straddle-mount region.

7. The method of claim 6 wherein said accumulating step includes the steps of:
   obtaining slot region reconstruction data corresponding to the shape of said slot region; and
   acquiring straddle-mount reconstruction data corresponding to the shape of said straddle-mount region.

8. The method of claim 7 wherein said accumulating step includes the step of:
   deriving composite structure data corresponding to said straddle-mount region, said deriving step deriving said composite structure data from said straddle-mount reconstruction data and said slot region reconstruction data, said slot region reconstruction data being used in said deriving step to confirm the accuracy of said straddle-mount reconstruction data.

9. A method of ultrasonic reconstructing and testing of a straddle-mount turbine rotor blade attachment structure including a slot region and a straddle-mount region, said method comprising the steps of:
   positioning ultrasound transducers in said slot region;
   scanning said slot region with said ultrasound transducers to produce slot region scan data;
   reconstructing said slot region based upon said slot region scan data to display slot region reconstruction data;
   positioning ultrasound transducers in said straddle-mount region;
   scanning said straddle-mount region with said ultrasound transducers to produce straddle-mount region scan data; and
   reconstructing said straddle-mount region based upon said straddle-mount region scan data to display straddle-mount region reconstruction data.

10. The method of claim 9 further comprising the step of:
    coordinating said slot region reconstruction data and said straddle-mount region reconstruction data to form composite structure data.

11. The method of claim 9 further comprising the step of:
    selecting test scan positions based upon said slot region reconstruction data.

12. The method of claim 11 further comprising the step of:
    executing ultrasonic test scans of said straddle-mount turbine rotor blade attachment structure at said test scan positions.

13. The method of claim 9 further comprising the step of:
    selecting test scan positions based upon said straddle-mount reconstruction data.

14. The method of claim 13 further comprising the step of:
    executing ultrasonic test scans of said straddle-mount turbine rotor blade attachment structure at said test scan positions.

15. The method of claim 10 further comprising the step of:
    selecting test scan positions based upon said composite structure data.

16. The method of claim 15 further comprising the step of:
    executing ultrasonic test scans of said straddle-mount turbine rotor blade attachment structure at said test scan positions.

* * * * *